United States Patent [19]
Rajala et al.

[11] Patent Number: 5,660,679
[45] Date of Patent: Aug. 26, 1997

[54] ROTARY SEALING SYSTEM

[75] Inventors: Gregory John Rajala, Neenah; Steven Craig Gehling, Oshkosh; Dean Edward Paszek, Wrightstown, all of Wis.

[73] Assignee: Kimberly-Clark Worldwide, Inc., Neenah, Wis.

[21] Appl. No.: 381,679

[22] Filed: Jan. 31, 1995

[51] Int. Cl.⁶ .................................................. B32B 31/00
[52] U.S. Cl. .................. 156/580.1; 156/582; 156/583.1; 425/174.2
[58] Field of Search .................. 156/73.1, 73.2, 156/73.3, 160, 163, 164, 229, 252, 253, 268, 290, 494, 495, 515, 516, 522, 580.1, 580.2, 581, 582, 583.1; 83/956, 30, 660; 264/442, 444; 425/174.2

[56] References Cited

U.S. PATENT DOCUMENTS

| | | | |
|---|---|---|---|
| 2,732,887 | 1/1956 | Drew et al. | 154/42 |
| 3,222,235 | 12/1965 | Buchner | 156/73 |
| 3,224,915 | 12/1965 | Balamuth et al. | 156/73 |
| 3,562,041 | 2/1971 | Robertson | 156/73 |
| 3,660,186 | 5/1972 | Sager et al. | 156/73 |
| 3,733,238 | 5/1973 | Long et al. | 156/580 |
| 3,890,892 | 6/1975 | Loose et al. | 101/32 |
| 3,939,033 | 2/1976 | Grgach et al. | 156/515 |
| 4,227,959 | 10/1980 | Brown | 156/515 |
| 4,305,240 | 12/1981 | Grevich et al. | 53/373 |
| 4,311,540 | 1/1982 | Hill | 156/73.1 |
| 4,394,208 | 7/1983 | Wang et al. | 156/580.1 |
| 4,404,052 | 9/1983 | Persson et al. | 156/73.1 |
| 4,478,659 | 10/1984 | Hall | 156/73.1 |
| 4,534,818 | 8/1985 | Kreager et al. | 156/466 |
| 4,650,530 | 3/1987 | Mahoney et al. | 156/73.1 |
| 4,697,117 | 9/1987 | Mishiro | 310/323 |
| 4,713,132 | 12/1987 | Abel et al. | 156/73.1 |
| 4,747,895 | 5/1988 | Wallerstein et al. | 156/73.3 |
| 4,758,293 | 7/1988 | Samida | 156/73.1 |
| 4,767,492 | 8/1988 | Fukusima et al. | 156/580.2 |
| 4,838,964 | 6/1989 | Thomsen et al. | 156/73.1 |
| 5,057,182 | 10/1991 | Wuchinich | 156/580.1 |
| 5,096,532 | 3/1992 | Neuwirth et al. | 156/580.1 |
| 5,110,403 | 5/1992 | Ehlert | 156/580.1 |
| 5,464,497 | 11/1995 | Unthank | 156/519 |
| 5,545,275 | 8/1996 | Herrin et al. | 156/731 |

FOREIGN PATENT DOCUMENTS

| | | |
|---|---|---|
| 760411 | 6/1967 | Canada. |
| 0251070 | 1/1988 | European Pat. Off.. |
| 1348018 | 11/1963 | France. |
| 2575447 | 7/1986 | France. |
| 1632007 | 8/1970 | Germany. |
| 423205 | 4/1967 | Switzerland. |
| 1314572 | 4/1973 | United Kingdom. |
| 2149343 | 6/1985 | United Kingdom. |
| 2162460 | 2/1986 | United Kingdom. |

*Primary Examiner*—James Sells
*Attorney, Agent, or Firm*—Mark L. Davis; Tom D. Wilhelm; Brian R. Tumm

[57] ABSTRACT

This invention pertains to apparatus and methods for processing workpieces on a moving continuous web using ultrasonic energy. The ultrasonic system includes one or more sets, each set containing first and second ultrasonic application devices, corresponding to an ultrasonic horn and a corresponding anvil. A first element of the set is mounted on a rotating work drum which carries the web of workpieces while the workpieces are being processed with ultrasonic energy. The second element of the set is mounted for rotation with the work drum. As the work drum rotates, the second element rotates with the drum. With each rotation of the work drum, the second element extends over the work drum and the first element, ultrasonic energy is applied to the workpiece, and the second element withdraws from over the work drum and the first element.

50 Claims, 8 Drawing Sheets

ROTARY SEALING SYSTEM

FIELD OF THE INVENTION

This invention relates to apparatus and methods for applying thermal energy to workpieces, such as for bonding, sealing, cutting and the like of the workpieces. More particularly, the present invention relates to an apparatus and method for applying ultrasonic energy to workpieces such as disposable diapers, training pants, feminine care products, feminine care and incontinence garments or the like.

BACKGROUND OF THE INVENTION

Use of mechanical vibration produced at an ultrasonic frequency to weld thermoplastics, and to emboss and form plastics is a well-established industrial process. The physical principles underlying this technology have important relations to the invention described herein and therefore merit brief review and discussion.

To obtain significant vibrational motion, most ultrasonic systems are operated at one of their frequencies of resonance. Both the ultrasonic generator and the ultrasonic horn are designed to resonate at the same frequency, in which case the vibration produced by the generator is communicated to the horn. Since the horn is tuned to the same frequency as the generator, the horn expands and contracts along its length in concert with the imposed motion of the vibration generator.

The motion produced at the free face of the horn is then reciprocal, or back and forth in a surface perpendicular to the surface of the horn, with an amplitude determined by the electrical voltage applied to the crystals of the vibration generator. It is known to condition the vibrations produced by the generator before the vibrations are communicated to the horn, including incorporating amplification devices and phase change devices into the sequence of elements so used.

One problem encountered in applying resonant ultrasonic vibration to continuous processes is the limitation on horn width. Although the horn executes motion principally of contraction and extension along its working surface, the wider the horn, e.g. the longer its working surface, typically the greater the variation in the amplitude of the vibrations along the length of the working surface. Accordingly, in general, use of ultrasonic energy to process workpieces in a continuous web has been limited to two types of processes.

The first type of process is one where a rotary ultrasonic horn disposed in a fixed location applies ultrasonic energy, against an underlying anvil, at essentially a line along a workpiece travelling, in a longitudinal direction along the workpiece, past the rotating horn. This first type of process is illustrated by U.S. Pat. 3,222,235 to Buchner.

The second type of process is one where one or more stationary flat planar surface or plunge-type, as they are commonly referred, ultrasonic horns extend across the width of the web and apply ultrasonic energy to all or selected parts of the web as the web passes between the stationary horns and corresponding underlying anvils, as illustrated by U.S. Pat. No. 3,939,033 to Grgach et al and U.S. Pat. No. 3,733,238 to Long et al, respectively. The plunge-type may imply its motion, however, the horn may, in fact, be stationary and the web moved to it.

In a first modification of the second type of process, U.S. Pat. No. 4,713,132 to Abel et al teaches mounting a series of flat planar surface horns for rotation about fixed axes disposed about a rotating anvil drum, and rotating the horns such that the horns rotate into and out of contact with the workpieces on the web.

In a second modification of the second type of process, U.S. Pat. No. 4,650,530 to Mahoney et al teaches folding the web of workpieces about the periphery of a rotating disc, and bringing ultrasonic horns, and corresponding anvils into alignment with the workpieces, as they rotate on the disc. The horns and anvils are of the flat planar surface arrangement. The horns and anvils rotate with the disc, and the ultrasonic system operates on the workpieces by bringing respective sets of horn and anvil against the respective workpiece at a locus in a free space between radially extending protrusions on the disc. Thus the disc which carries the workpieces does not participate in the application of ultrasonic energy, and the reciprocating motion of the ultrasonic horns operates in a direction coincident with the direction of extension of the axis of the rotating disc which carries the workpieces.

A second problem with flat planar surface ultrasonic horns is that, in order to obtain uniform application of the ultrasonic energy along the length of the horn, the spacing of the horn from the anvil must be aligned in two dimensions along the face of the horn such that the working surface of the horn is e.g. precisely parallel with the working surface of the anvil. Especially where there is e.g. any continuing motion of the horn or the anvil other than the ultrasonic vibrations, for example rotation of either or both of the horn or anvil, such precise alignment becomes a dynamic problem, requiring constant monitoring and repeated adjustment of the spacing between the horn and the anvil.

It is an object of this invention to provide an ultrasonic system including an ultrasonic horn and a cooperating anvil wherein one of the horn and anvil is mounted on a rotating web-carrying work drum, and the other of the horn and anvil is mounted for rotation with the work drum, and to extend over the work drum to apply ultrasonic energy to a workpiece and to withdraw from over the work drum during each rotation of the work drum.

It is another object to provide an ultrasonic system wherein the anvil is mounted on the work drum and the ultrasonic horn is mounted for rotation with the work drum, and for extending over the work drum and withdrawing from over the work drum during each rotation of the work drum.

It is still another object to provide an ultrasonic system wherein the horn is a rotary ultrasonic horn adapted to traverse across the width of the workpiece web, applying pressure and ultrasonic energy, thus to provide line application of ultrasonic energy to the workpiece, moving progressively across the workpiece on the web.

Still another object is to provide such a system including a plurality of sets of horns and anvils disposed about the circumference of the work drum, wherein the system can simultaneously process a related plurality of workpieces.

Yet another object is to provide an ultrasonic system wherein one or more ultrasonic horns of the plunge type are mounted on the rotating work drum, and a corresponding anvil is mounted for rotation with the work drum, and for extending over the work drum and withdrawing from over the work drum during each rotation of the work drum.

A further object is to provide an ultrasonic system wherein one or more ultrasonic horns of the plunge type are mounted on the rotating work drum and the respective anvil is a rotating anvil adapted to traverse across the width of the workpiece web, applying pressure against the respective horn, thus to provide line application of ultrasonic energy to the workpiece, moving progressively across the web.

SUMMARY OF THE INVENTION

This invention describes a thermal energy system for applying ultrasonic energy to a workpiece, the system comprising a drum, mounted for rotation about a first axis in a given direction, the drum having a circumferential outer working surface; a first ultrasonic application device, mounted on the drum at the outer working surface, and extending transverse to the direction of rotation of the drum; and a second ultrasonic application device, mounted for rotation with the drum, and for moving in a direction transverse to the direction of rotation of the drum to thereby extend over the first ultrasonic application device, and operate in combination with the first ultrasonic application device, to apply ultrasonic energy to the workpiece during rotation of the drum, and for subsequently withdrawing from over the first ultrasonic application device during rotation of the drum, one of the first and second ultrasonic application devices comprising an ultrasonic horn adapted to provide ultrasonic energy, the other of the ultrasonic application devices comprising an anvil adapted to cooperate with the ultrasonic horn.

In a first family of embodiments of the ultrasonic system, the first ultrasonic application device comprises the anvil, and the second ultrasonic application device comprises the ultrasonic horn. The anvil may comprise a metal bar mounted flush with the outer working surface of the drum.

The ultrasonic horn is preferably mounted to extend over the anvil, to apply downward pressure on a workpiece on the anvil, thereby to apply ultrasonic energy to the workpiece while being extended over the anvil, and to subsequently withdraw from over the anvil, during each 360 degree rotation of the drum.

The ultrasonic horn may be mounted to traverse an energy application path over the anvil and a workpiece on the anvil, the energy application path being oriented transversely across the outer working surface, the ultrasonic system preferably further comprising apparatus for simultaneously applying pressure and ultrasonic energy through the ultrasonic horn, to the workpiece disposed on the anvil, thereby to accomplish work on the workpiece while the ultrasonic horn is so traversing the energy application path.

In preferred ones of this first family of embodiments, the ultrasonic horn comprises a wheel, thus a rotary ultrasonic horn, mounted for rotation about a second axis, to thereby apply ultrasonic energy to the workpiece at a point progressively moving across the workpiece as the ultrasonic horn traverses the energy application path. The energy application path may include an outgoing segment wherein the rotary ultrasonic horn is extended over the anvil and an incoming segment wherein the rotary ultrasonic horn is withdrawn from over the anvil, the ultrasonic system further comprising apparatus for applying pressure through the rotary ultrasonic horn to the workpiece as the ultrasonic horn traverses the energy application path, and control apparatus adapted to activate the apparatus for applying pressure, to thereby apply pressure through the rotary ultrasonic horn to the workpiece on one of the segments of the energy application path, preferably the outgoing segment, and to withhold the pressure on the other of the segments of the energy application path.

Also in preferred ones of this first family of embodiments, the ultrasonic system comprises at least two, or more, of the anvils mounted essentially at different radial locations about the outer working surface of the drum, and corresponding at least two of the ultrasonic horns, preferably rotary ultrasonic horns, mounted for rotation with the drum and over respective ones of the at least two anvils, the control apparatus including apparatus for controlling operation of all of the at least two ultrasonic horns such that the respective ultrasonic horn begins being extended over a respective one of the anvils when the respective anvil is disposed at a locus corresponding to a first angle "E" measured with respect to a reference line passing through the first axis of rotation and subsequently withdraws from over the respective said anvil such that said rotary ultrasonic horn is fully withdrawn from over the respective anvil when the drum has rotated such that the respective anvil is disposed at a locus corresponding to a second angle "W" measured with respect to the reference line passing through the first axis of rotation, and wherein the same angles "E" and "W" apply for each of the at least two ultrasonic horns.

In a second family of embodiments of the ultrasonic system, the first ultrasonic application device comprises the ultrasonic horn, and the second ultrasonic application device comprises the anvil. In this second family of embodiments, the ultrasonic horn typically comprises a plunge-type ultrasonic horn, having an ultrasonic working surface mounted essentially flush with the outer working surface of the drum.

The anvil is mounted to extend over the ultrasonic horn, to apply pressure on a workpiece on the ultrasonic horn, and thereby to apply ultrasonic energy to the workpiece while being extended over the ultrasonic horn, and accomplish work on the workpiece while so traversing the ultrasonic horn, and to subsequently withdraw from over the ultrasonic horn, during each 360 degree rotation of the drum.

In preferred embodiments, the anvil comprises a wheel mounted for rotation about a second axis, thus a rotary anvil, such that the combination of the anvil and the ultrasonic horn provides effective ultrasonic energy to the workpiece at a line moving progressively across the workpiece as the anvil traverses the energy application path. The energy application path may include an outgoing segment wherein the rotary anvil is being extended over the ultrasonic horn and an incoming segment wherein the anvil is withdrawn from over the ultrasonic horn, the ultrasonic system further comprising apparatus for applying pressure through the rotary anvil to the workpiece as the workpiece traverses the energy application path, and control apparatus adapted to activate the apparatus for applying pressure, to thereby apply pressure through the rotary anvil to the workpiece on one of the segments, preferably the outgoing segment, of the energy application path and to withhold the pressure on the other of the segments of the energy application path.

The ultrasonic system may further comprise at least two ultrasonic horns mounted at different radial locations about the outer working surface of the drum, and corresponding at least two anvils, preferably rotary anvils, mounted for rotation with the drum and over respective ones of the at least two ultrasonic horns, the control apparatus including apparatus for controlling operation of all of the at least two anvils such that the respective anvil begins being extended over a respective ultrasonic horn when the respective anvil is disposed at a locus corresponding to a first angle "E" measured with respect to a reference line passing through the first axis of rotation and subsequently withdraws from over the respective anvil such that the rotary ultrasonic horn is fully withdrawn from over the respective ultrasonic horn when the drum has rotated such that the respective ultrasonic horn is disposed at a second angle "W" measured with respect to the reference line passing through the first axis of rotation, and wherein the same angles "E" and "W" apply for each of the at least two ultrasonic horns.

In a third family of embodiments of the ultrasonic system of the invention, the system further comprises placing apparatus adjacent the drum, at a placing station disposed at an angle "P" measured with respect to a reference line passing through the first axis, for placing a workpiece onto a working station of the outer working surface where ultrasonic energy can be applied to the workpiece by the first and second ultrasonic application devices; removing apparatus adjacent the drum, at a removing station disposed at an angle "R" measured with respect to the reference line passing through the first axis, for removing the workpiece from the outer working surface, such that the workpiece traverses a working path on the outer working surface essentially about the circumference of the drum from the placing station to the removing station; and control apparatus for controlling movement of the second ultrasonic application device such that the second ultrasonic application device extends over the drum and correspondingly over the first ultrasonic application device and the workpiece while the workpiece traverses the working path and withdraws from over the drum and the first ultrasonic application device while the working station of the outer working surface traverses from the removing station to the placing station.

In a fourth family of embodiments, the invention comprehends a method comprising the steps of rotating a drum about a first axis in a given direction, the drum having a circumferential outer working surface, a first ultrasonic application device mounted on the drum at the outer working surface and extending transverse to the direction of rotation of the drum; providing a second ultrasonic application device, mounted for rotation with the drum; moving the second ultrasonic application device in a direction transverse to the direction of rotation of the drum and thereby extending the second ultrasonic application device over the first ultrasonic application device and operating the first and second ultrasonic application devices in combination and thereby applying ultrasonic energy to the workpiece during rotation of the drum; and withdrawing the second ultrasonic application device from over the first ultrasonic application device during rotation of the drum, one of the first and second ultrasonic application devices comprising an ultrasonic horn adapted to provide ultrasonic energy, the other of the ultrasonic application devices comprising an anvil adapted to cooperate with the ultrasonic horn.

The method preferably includes extending the second ultrasonic application device over the first ultrasonic application device, applying pressure on a workpiece on the first ultrasonic application device, and thereby applying ultrasonic energy to the workpiece, and accomplishing work on the workpiece while the second ultrasonic application device is so traversing the energy application path, and subsequently withdrawing the second ultrasonic application device from over the first ultrasonic application device, during each 360 degree rotation of the drum.

The first ultrasonic application device may comprise an anvil, with the second ultrasonic application device comprising a rotary ultrasonic horn, e.g. a wheel, mounted for rotation about a second axis, namely a rotary anvil, with the method comprising applying ultrasonic energy to the workpiece at a line moving progressively across the workpiece as the second ultrasonic application device traverses the energy application path.

Preferably, the method comprehends applying pressure, through the second ultrasonic application device to the workpiece as the second ultrasonic application device traverses the energy application path. The energy application path permissively includes an outgoing segment wherein the second ultrasonic application device, e.g. a rotary ultrasonic horn, is extended over the first ultrasonic application device and an incoming segment wherein the second ultrasonic application device is withdrawn from over the first ultrasonic application device, whereupon the method may further comprise controlling the second ultrasonic application device and thereby applying pressure through the second ultrasonic application device to the workpiece on one of the segments of the energy application path, preferably the outgoing segment, and withholding the pressure on the other of the segments of the energy application path.

The method permissively operates in an ultrasonic system comprising at least two first ultrasonic application devices mounted at different radial locations about the outer working surface of the drum, and corresponding at least two second ultrasonic application devices mounted for rotation with the drum and over respective ones of the at least two first ultrasonic application devices, and including controlling operation of all of the at least two second ultrasonic application devices and thereby beginning to extend each second ultrasonic application device over a respective first ultrasonic application device when the respective first ultrasonic application device is disposed at a locus corresponding to a first angle "E" measured with respect to a reference line passing through the first axis of rotation, rotating the drum, and subsequently withdrawing the respective second ultrasonic application device from over the respective first ultrasonic application device such that the second ultrasonic application device is fully withdrawn from over the first ultrasonic application device when the drum has rotated such that the respective first ultrasonic application device is disposed at a second angle "W" measured with respect to the reference line passing through the first axis of rotation, and wherein the same angles "E" and "W" measured with respect to the reference line passing through the first axis of rotation, apply for each of the at least two second ultrasonic application devices.

The method may include placing a workpiece onto a working station of the outer working surface at an angle "P" measured with respect to a reference line passing through the first axis; rotating the drum; while rotating the drum, controlling movement of the second ultrasonic application device and thereby extending the second ultrasonic application device over the drum and correspondingly over the workpiece; and withdrawing the second ultrasonic application device from over the drum such that the second ultrasonic application device is withdrawn from over the drum while the working station of the outer working surface traverses from the removing station to the placing station.

BRIEF DESCRIPTION OF THE DRAWINGS

The present invention will be more fully understood and further advantages will become apparent when reference is made to the following detailed description of the illustrated embodiments and the drawings, in which.

DETAILED DESCRIPTION OF THE ILLUSTRATED EMBODIMENTS

The following detailed description of the illustrated embodiments is made in the context of making disposable type garments such as diapers, training pants, feminine care products, incontinence garments, and the like, and includes apparatus and methods for joining two superposed spunbonded polypropylene elasticized composite webs, e.g. 0.7 ounce per square yard each, by producing ultrasonic welds at spaced locations extending across the webs in directions transverse (cross machine direction) to the direction of travel of the webs in the processing apparatus (with machine direction). The specific context is the production of disposable type garments in a continuous combined web, where the garment preforms in the web extend transverse to the web, with the waist portions of the garments extending along the machine direction of the web, and the front and back portions of the garments being on opposing sides of the web. In the embodiments illustrated, the welds join the superposed webs at locations generally corresponding to the ultimate locations of side seams in the finished garments.

Figure 1:
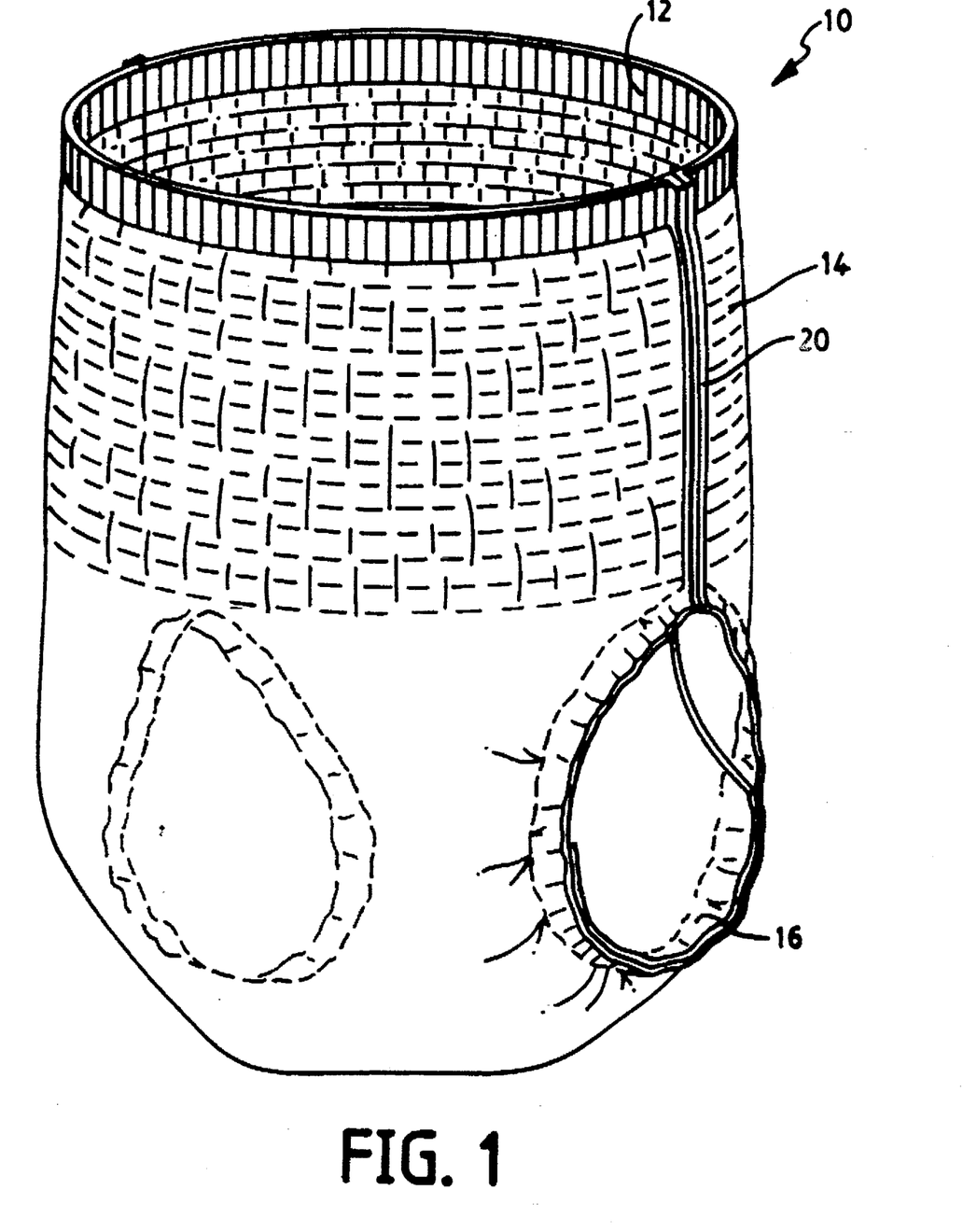
FIG. 1 is a perspective view of a workpiece which may be made using methods and apparatus of this invention.

It is generally known to make a garment 10 of the type shown in FIG. 1. Such garments typically comprise an assemblage of two or more layers or partial layers of different materials or may comprise substantially the same materials, along with other elements. Typically, the material is a woven or non-woven fabric, or a polymer film. Elastic may be used at the waist 12, in the body portion 14, and around the leg openings 16.

Figure 2:
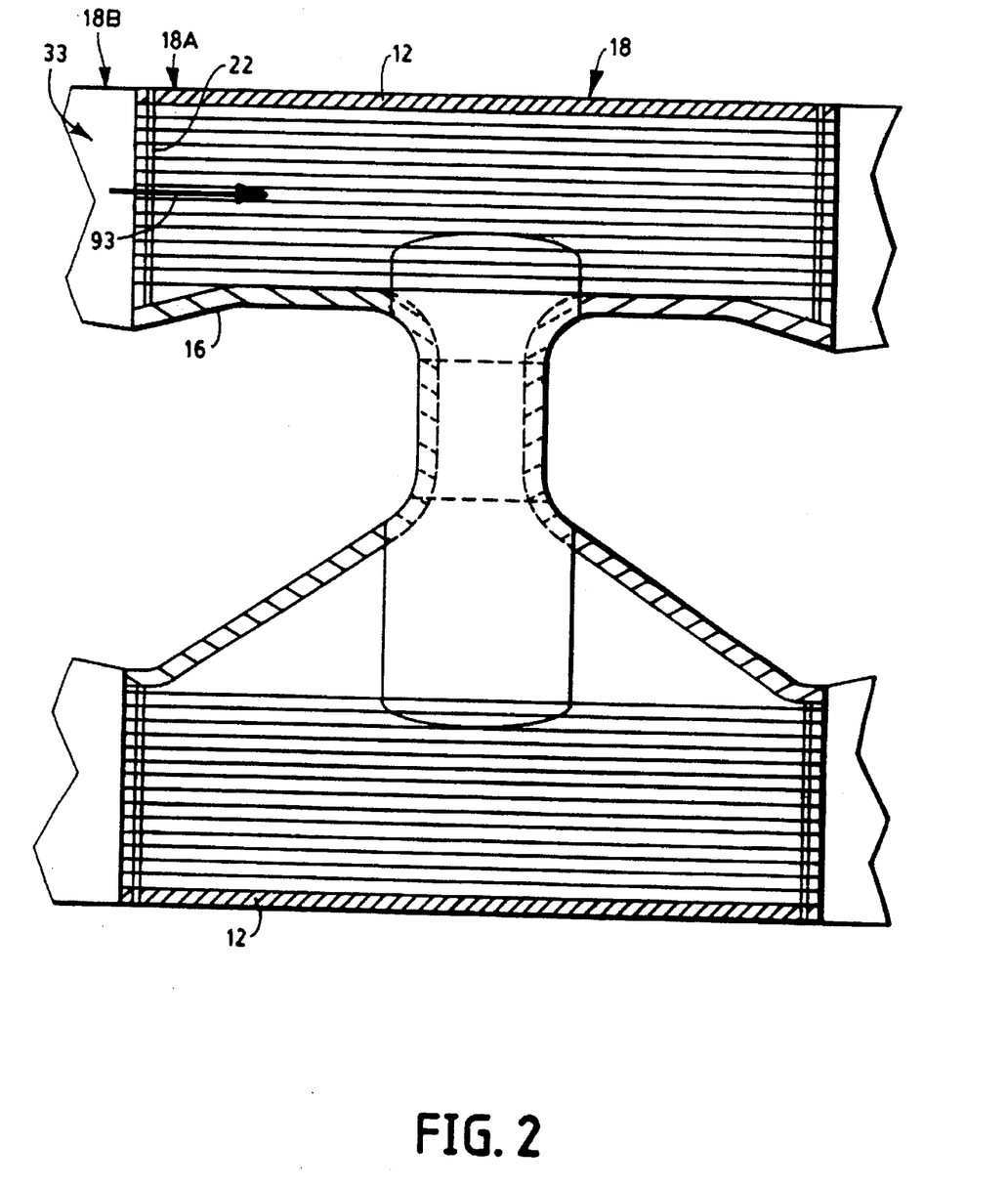
FIG. 2 is a top view of a finished workpiece blank, as a workpiece in a continuous web, from which the workpiece of FIG. 1 can be made.

In this context, as in most such processes for fabricating the garment as at 10, a blank 18 such as that shown in FIG. 2 is first made as part of a continuously processed composite web of materials. After the blank is fully fabricated, the sideseams 20 are formed and the garment is severed from the web either as a blank, fully finished or partially finished, or as a fully formed garment article.

The process contemplated by the invention forms the welds 22 adjacent the adjoining edges of leading and trailing blanks 18A and 18B as illustrated in FIG. 2. In forming such transverse welds using known technology, it is difficult to obtain uniform application of thermal energy across the entire width of the web, whereby the welds may exhibit less than the desired uniformity. The apparatus and methods disclosed hereinafter provide a novel approach to achieving predictably uniform such welds in the blanks being formed.

FIGS. 3–7 illustrate one embodiment of a thermal system of the invention. Said thermal energy system may be comprised of any device by which the transfer of thermal energy is sufficient to weld the material together, such as electrical resistance devices such as continuously heated or intermittently heated impulse type devices, or induction heated components. The preferable thermal energy source is by the use of ultrasonics. As seen there, an ultrasonic system 24 includes a work drum 26 mounted on an outer shaft 25, for rotation about an axis 28 passing through a fixed inner shaft generally designated as 30. The work drum 26 has an outer working surface 32 perforated and otherwise adapted in conventional manner (not shown) to provide suction through the outer working surface of the work drum 26, to hold a web 33 of material workpieces which, when all processing is finished, can be assembled as blanks 18 into the garment articles 10.

A plurality of anvil bars 34 (six are shown) are mounted to the work drum, spaced uniformly about the outer circumference of the work drum, and extend transversely across the width dimension of the outer working surface of the work drum 26. The anvil bars are flush with the outer working surface 32, such that outer surfaces 36 of the anvil bars 34 generally comprise a continuation of the outer working surface 32 of the work drum 26.

Figure 4:
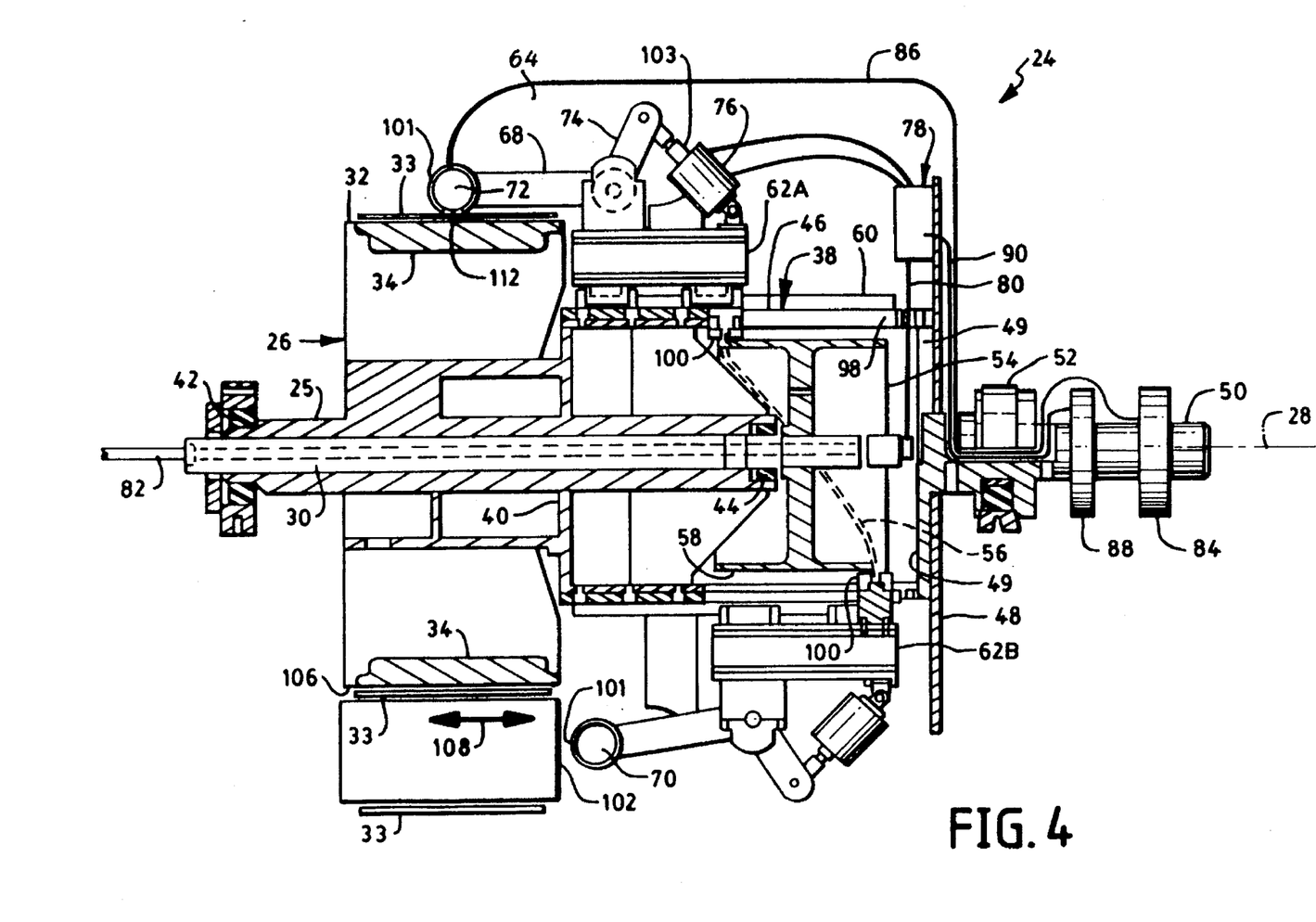
FIG. 4 is a cross-section of the thermal energy system of FIG. 3, taken at planar section 4—4 of FIG. 3.

A support drum 38 is secured to the work drum 26, and mounted for rotation with the work drum. Referring to FIG. 4, support drum 38 is secured to work drum 26 at interface wall 40. The combination of the work drum 26 and the support drum 38 are mounted to the outer shaft 25. Outer shaft 25 is mounted to the fixed inner shaft 30 by bearings 42 and 44. An outer wall 46 of the support drum 38 is secured to end flange 48 through end wall 49. End flange 48 is secured to driven shaft 50 which is driven off the line shaft, not shown, of the processing line. Driven shaft 50 is mounted to ground through bearing 52. Accordingly, the work drum 26, the support drum 38, and the end flange 48 are all supported by the combination of bearings 42, 44, and 52, and all rotate in unison about fixed inner shaft 30 and the axis 28.

Cam drum 54 is fixedly secured to fixed inner shaft 30, such that it does not rotate with the combination of work drum 26, support drum 38, and end flange 48. Cam rib 56 is mounted on the outer wall 58 of the cam drum 54, and extends about the entire circumference of the outer wall 58 of the cam drum. Cam rib 56 is seen in dashed outline in FIGS. 4 and 8. A portion of the cam rib is seen through a cutaway portion of the outer wall 46 of the support drum in FIG. 3.

Six pairs of carriage support tracks 60 are secured to the outer wall 58 of cam drum 54, corresponding in number, and in general location, to respective anvil bars 34 on the outer working surface 32 of work drum 26. A carriage 62 is mounted to each pair of carriage support tracks 60, for sliding engagement with the carriage support tracks, along the lengths "L" of the respective carriage support tracks, as will be illustrated further hereinafter.

Figure 6:
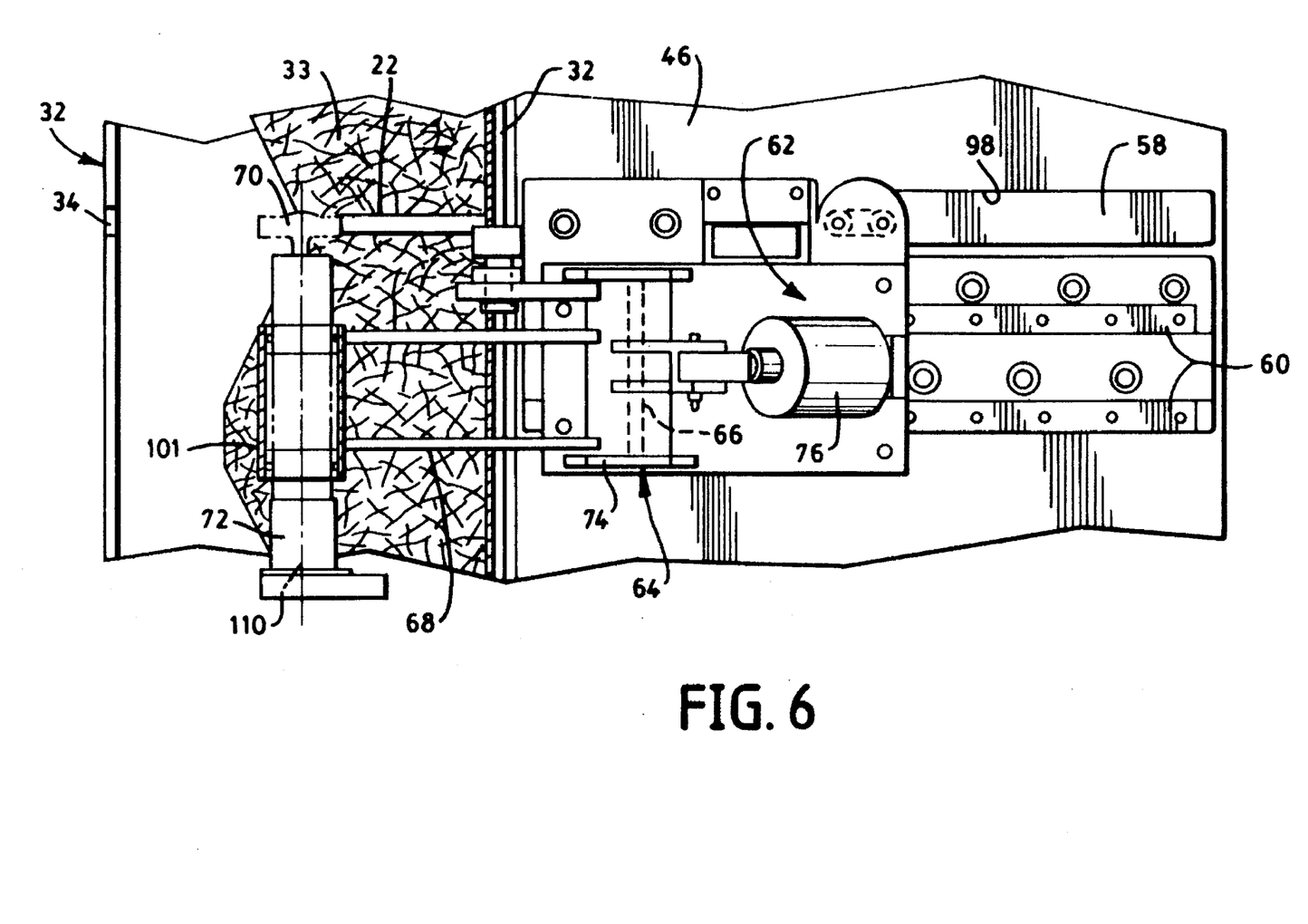
FIG. 6 is a top view of the first thermal energy application device, taken at 6—6 of FIG. 3.
Figure 7:
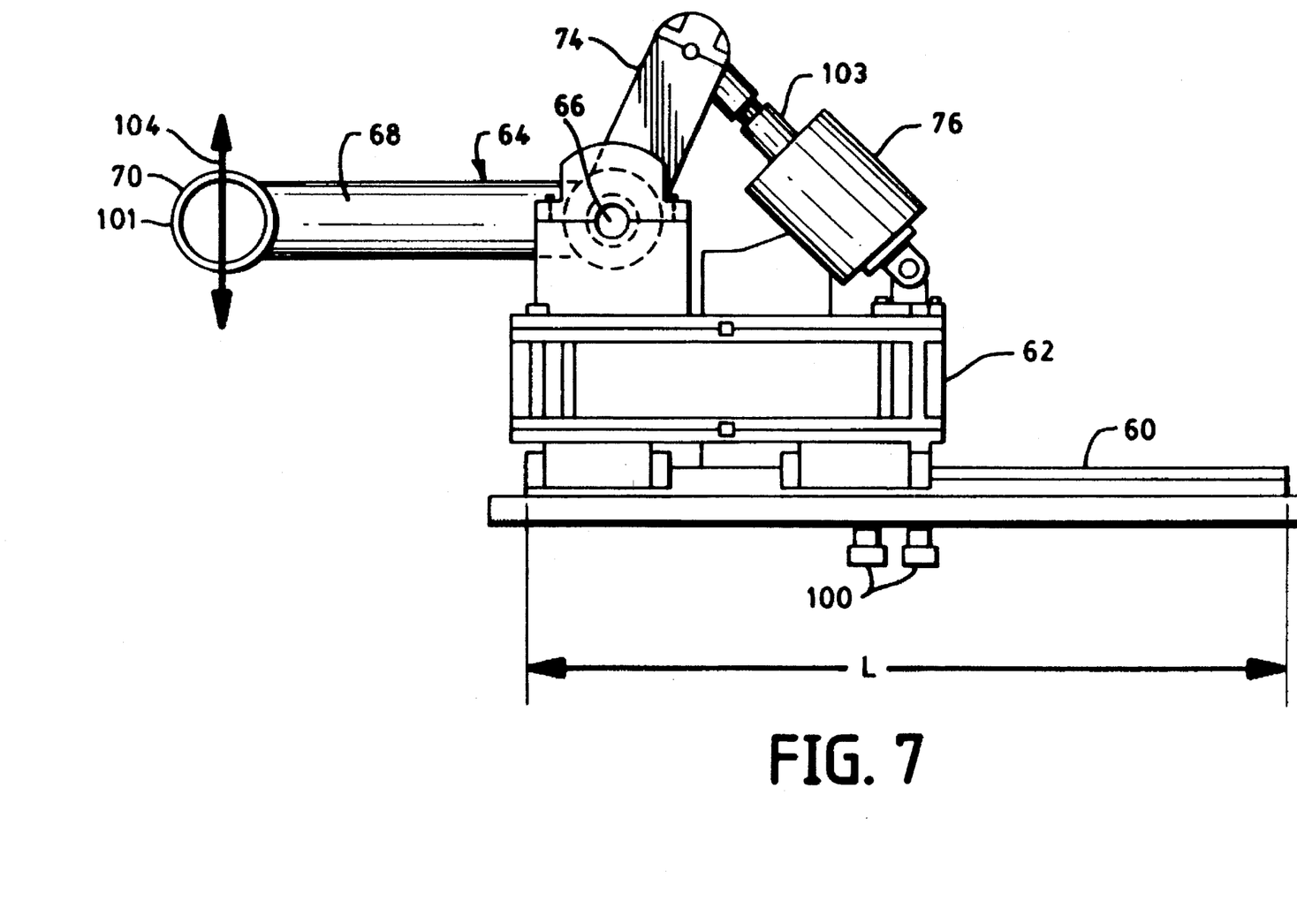
FIG. 7 is a side view of the first thermal energy application device of FIG. 6.

Referring now to FIGS. 6 and 7, an ultrasonic support subassembly 64 is mounted to each carriage 62 at pivot pin 66. In the ultrasonic support subassembly 64, support arm 68 extends from pivot pin 66, toward outer working surface 32 of the work drum 26, and supports, at its remote end, a rotary ultrasonic horn 70 and ultrasonic generator 72. Support arm 68 is fixedly secured to control arm 74. Control arm 74 is operated by double acting air cylinder 76, acting through pivot pin 66 and control arm 74, to pivot the ultrasonic horn 70 about pivot pin 66 and thereby to raise and lower the ultrasonic horn 70 with respect to the outer working surface 32 of work drum 26. Thus, the ultrasonic support subassembly 64 comprises pivot pin 66, support arm 68, and control arm 74.

Compressed air is supplied to the air cylinder 76 from pneumatic control box 78. See FIG. 4. Compressed air is supplied to the pneumatic control box 78 through supply line 80, which is connected, through a conventional rotary pneumatic coupling to fixed shaft 30. Air is supplied through the center of fixed shaft 30 from a supply line 82.

Electric power is supplied to the ultrasonic system 24 through slip rings 84, and is communicated to the ultrasonic generators through supply line 86.

Programmable limit switch 88 is also mounted to the driven shaft 50, for purpose to be discussed hereinafter. Output of the programmable limit switch 88 is fed to the control box 78 through electric line 90.

It is contemplated that the operation and functions of the invention have become fully apparent from the foregoing description of elements and their relationships with each other, but for completeness of disclosure, the usage of the invention will be briefly described.

Turning now to FIG. 4, driven shaft 50 turns end flange 48, work drum 26, support drum 38 and its supported carriages 62, ultrasonic support subassemblies 64, ultrasonic horns 70, and generators 72, continuously at a steady speed of rotation. An incoming turning roll 92 is disposed at a placing station, relative to a reference line through axis 28, at an angle "P" on the circumference of the work drum 26. A web 33 of workpieces or other material is fed, in the direction indicated by arrow 93 about incoming turning roll 92, and is thereby drawn into engagement with the working surface 32 of the work drum 26, at the nip formed between work drum 26 and turning roll 92, while the work drum is rotating in the direction indicated by the arrow 94. The web 33 is generally drawn about the circumference of work drum 26 at its outer working surface from incoming turning roll 92 until it reaches the outgoing turning roll 96, at the removing station disposed at an angle "R" on the circumference of the work drum. At outgoing turning roll 96, the web 33 turns about the turning roll 96 as indicated there by the web 33, and is thus removed from the work drum and exits the process of interest in this invention.

In general, as the invention is practiced, the ultrasonic horns are continuously activated, resonating at their designed frequencies.

Turning to the combination of FIGS. 3–7, a slot opening 98 extends through the outer wall 46 of support drum 38 adjacent each carriage support track 60. A pair of cam followers 100 extends downwardly from each respective carriage, through slot opening 98, and engages the rib cam 56. Accordingly, as the working drum and support drum rotate on axis 28, about the stationary cam drum 54, the engagement of the cam followers 100 with the rib cam 56 causes the carriages 62 to move alternately toward and away from the outer working surface 32 of the work drum 26. Each carriage thus makes one complete round trip motion, toward the work drum and away from the work drum, for each 360 degree rotation of the work drum. Accordingly, and now referring to FIGS. 3–5, the carriage 62A at the 12 o'clock position on support drum 38 is fully extended toward the work drum; and the carriage 62B at the 6 o'clock position on support drum 38 is fully withdrawn away from the work drum.

Figure 3:
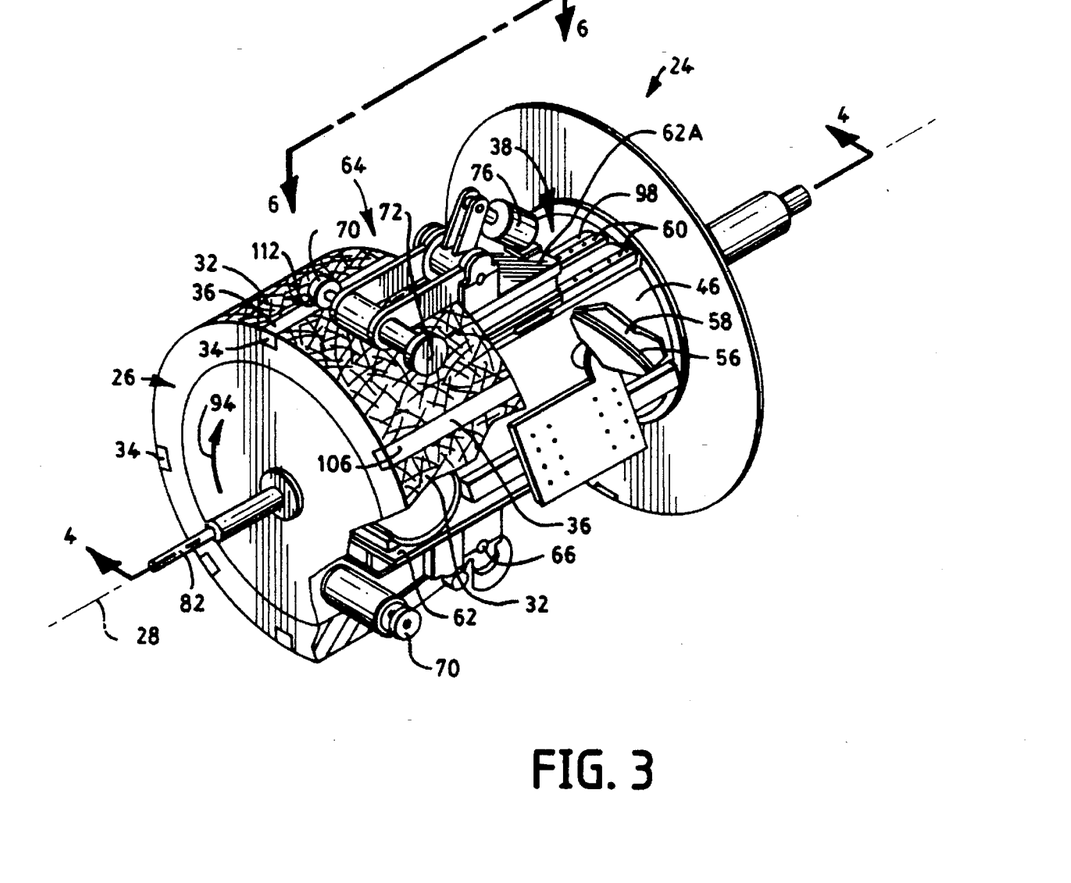
FIG. 3 is a pictorial view, with parts missing and parts cut away, showing a thermal energy system of the invention.
Figure 5:
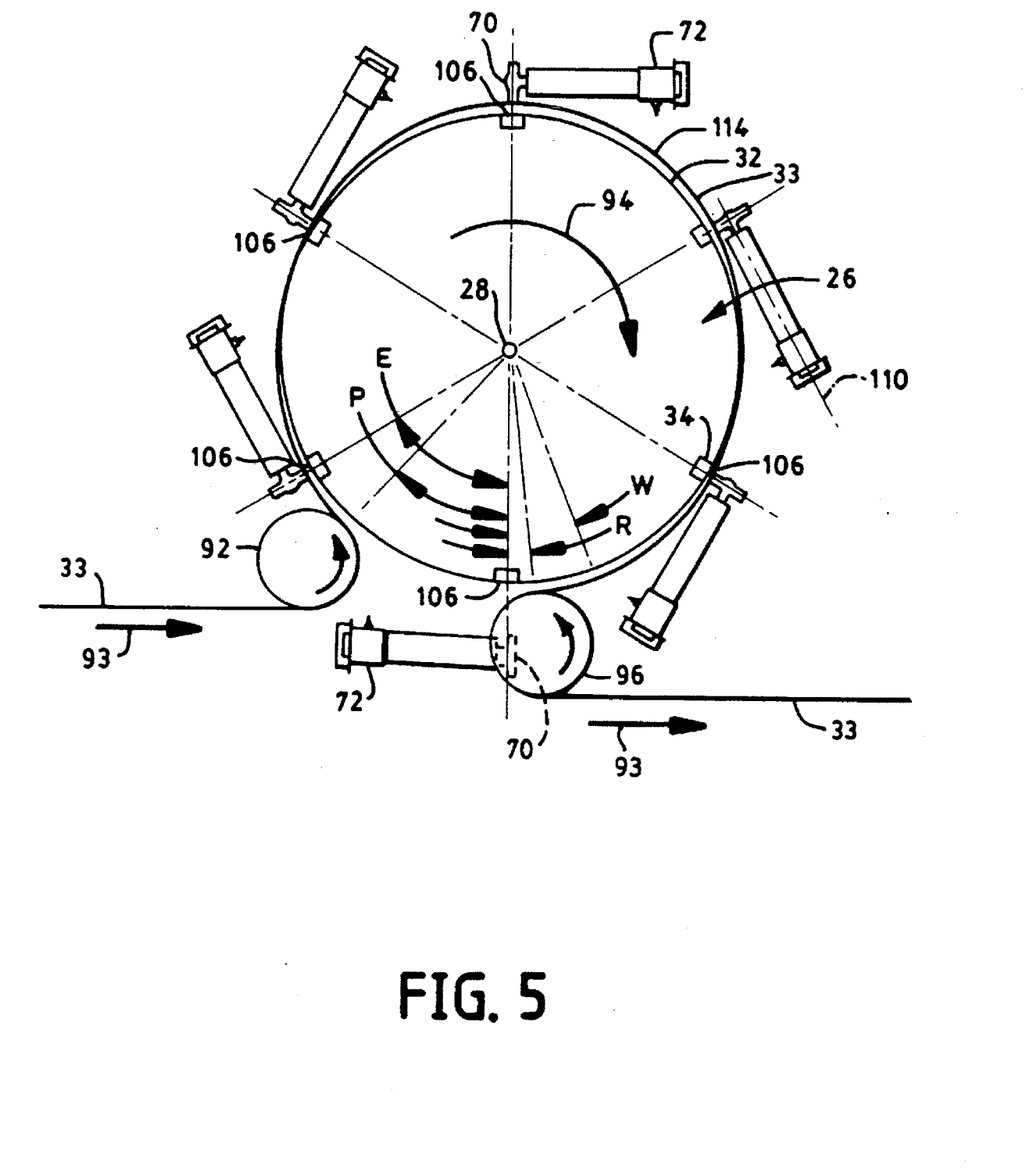
FIG. 5 is a schematic representation of an end elevation view of the thermal energy system of FIG. 3.

As the carriages extend toward the work drum 26, the respective ultrasonic horns extend over the outer working surface 32 of the work drum, and over the corresponding anvil bar 34. As the carriages withdraw from the work drum, the respective ultrasonic horns withdraw from over the outer working surface of the work drum.

An ultrasonic horn is considered fully withdrawn from over the outer working surface 32 when the remote outer edge 101 of the combination of the ultrasonic support assembly 64, horn 70, and generator 72, passes inwardly of the inner edges 102 of turning rolls 92 and 96. See FIG. 4, where the horn on carriage 62B is fully withdrawn, and has moved still further away from the work drum than the defined "fully withdrawn" position. Accordingly, "fully withdrawn" comprehends a range of positions of the outer edge 101 disposed inwardly of the inner edges 102 of the turning rolls 92 and 96, and is not limited to the innermost position where the carriage 62 is disposed in its most remote position with respect to the work drum.

As each carriage 62 extends toward the work drum, and the respective ultrasonic horn 70 is correspondingly disposed over the outer working surface 32, programmable limit switch 88 signals the pneumatic control box 78, thus activating and extending the ram 103 on the respective air cylinder 76 to thus move the respective resonating ultrasonic horn 70 downwardly, as shown by the double headed arrow indicated as 104 in FIG. 7, and into contact with the workpiece being carried in the web 33 at the respective work station 106 defined at each respective anvil bar 34. The rotary ultrasonic horn 70 exerts a downward force on the workpiece against the supporting resistance of the anvil bar. The amount of downward force is controlled by the force exerted at air cylinder 76.

With the resonating rotary ultrasonic horn thus exerting a downward force on the workpiece, the circular rotary horn 70 is allowed to rotate about an axis 110 as it provides an effective application of ultrasonic energy to the workpiece at a point 112 moving progressively across the workpiece as the ultrasonic horn traverses across the working surface in an energy application path 108. As indicated in FIG. 4, the energy application path can extend less than all the way across the web; or can extend all the way across the web, depending on what work is to be performed by the ultrasonic energy, and the lengths of carriage support tracks 60 and support arm 68.

Preferably, the ultrasonic horn 70 is forced downwardly into working contact with the workpiece while the horn is traversing the outgoing segment of the energy application path. When the respective ultrasonic horn reaches the outer extremity of the outgoing segment of the energy application path, limit switch 88 senses the respective associated angular position of the working station with respect to axis 28, and signals the pneumatic control box 78, lifting the horn from the workpiece as the horn is being withdrawn from over the workpiece on the (reverse direction) incoming segment of the energy application path. Referring to FIG. 5, the horn begins being extended over the drum, namely crossing the inner edge 102 of the turning rolls 92, 96 at an angle "E" on the outer circumference of the work drum, and is fully withdrawn from over the outer working surface at an angle "W" on the outer circumference of the work drum. Referring to FIG. 5, it is seen that the respective horn assembly is fully withdrawn before the respective workpiece in web 33 arrives at the turning roll 96 where the workpiece and web are removed from the work drum 26. Similarly, the horn assembly, comprising horn 70, generator 72, and ultrasonic support subassembly 64, remains fully withdrawn, and does not begin being extended over the outer working surface 32 until the horn assembly has passed the incoming turning roll 92 and the outer working surface is again becoming engaged with the incoming web of workpieces.

The working drum 26 thus rotates continuously, accompanied by the ultrasonic horns 70. Workpieces enter the ultrasonic system 24 as they are placed on the work drum 26 as part of web 33, and traverse the working path 114 between the placing station at angle "P" and the removing station at an angle "R," while the ultrasonic application devices, as horns 70 and anvils 34, form the welds 22. Each horn thus extends across the outer working surface at the respective anvil to make a weld in the workpiece with each rotation of the work drum. The welds 22 extend in the cross machine direction. At any given time, the combined apparatus can support performing welding, cutting, or the like operations on substantially as many workpieces as there are work stations 106, and corresponding workpieces, on the drum between the turning rolls 92 and 96, allowing sufficient clearance for "full withdrawal" of the respective horns from the outer working surface so that the web with the finished workpieces can be removed at turning roll 96.

Suitable rotary ultrasonic horns 70 are, for example, those taught in U.S. Pat. No. 5,110,403 to Ehlert, herein incorporated by reference for its teaching with respect to suitable such rotary ultrasonic horns. Suitable ultrasonic generators, and other related ultrasonic equipment, is available from a variety of suppliers, for example, Sonic Power Company, Danbury, Conn.

Figure 8:
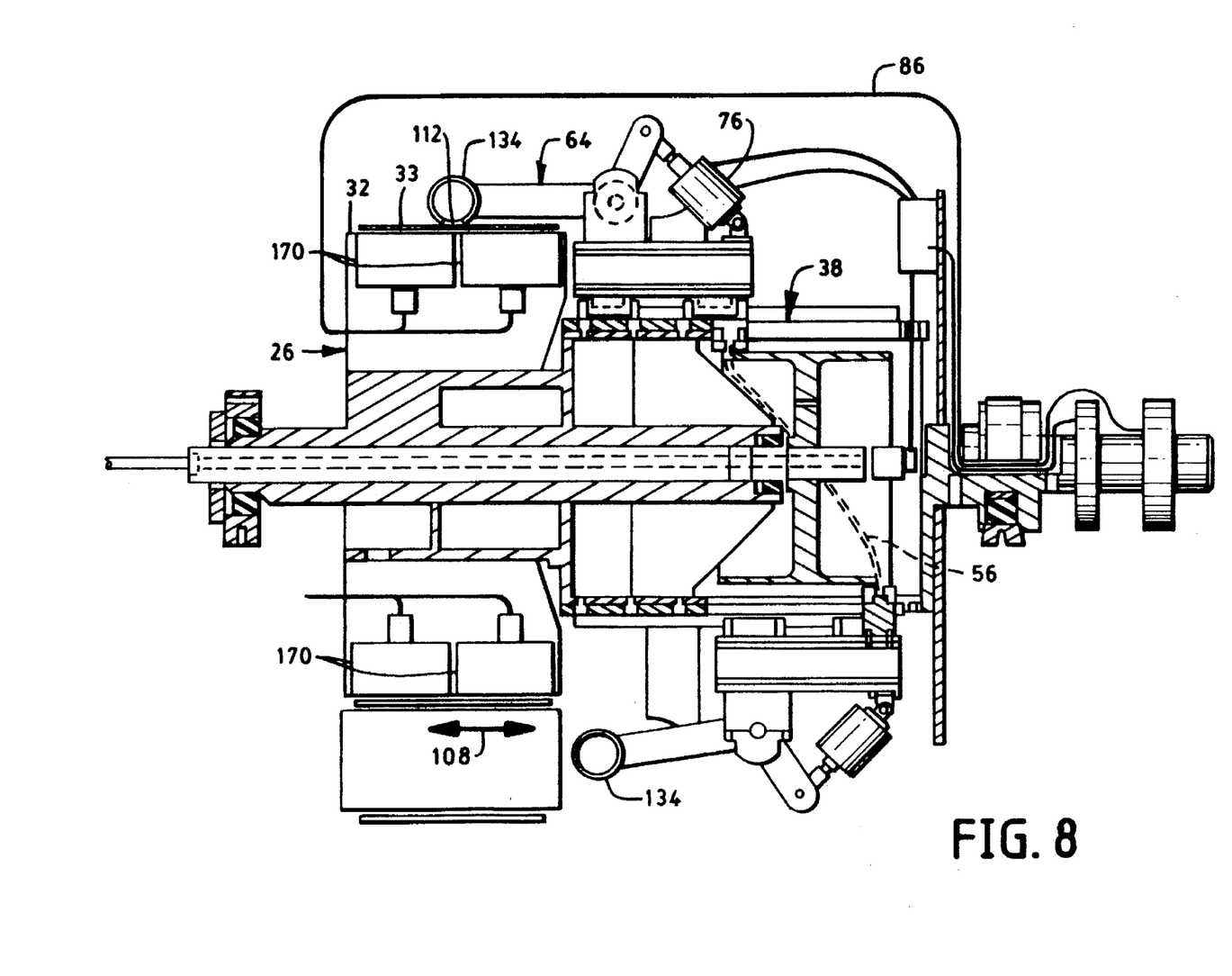
FIG. 8 is a cross-section as in FIG. 4, of a second embodiment of thermal energy systems of the invention.

FIG. 8 shows a second embodiment of the invention wherein the ultrasonic horn and the cooperating anvil are disposed in physically reversed locations from the embodiment of FIGS. 3-7. Thus, comparing the embodiment of FIG. 8 to the embodiment described in more detail with respect to FIGS. 3-7, in FIG. 8, a pair of conventional plunge-type ultrasonic horns 170 are mounted in the work drum 26 in place of the anvil bar 34. As many plunge type horns can be used as necessary to span the full width of the energy application path. Correspondingly, a rotary anvil 134 is mounted to the ultrasonic support assembly 64 in place of the rotary ultrasonic horn 70.

In use, the ultrasonic horns 170 are preferably activated continuously during operation of the process. Work drum 26 and support drum 38 rotate continuously as described above. As the drums rotate, the anvil is extended over the working surface, and forced into working contact with the workpieces by air cylinder 76 as the anvil traverses the outgoing segment of the energy application path 108, and lifts the anvil from the workpiece as it traverses the incoming segment of the energy application path. The significant difference is that the locations of the ultrasonic horn and the anvil are reversed, while the physical movement role of extending over the outer working surface and subsequently withdrawing remains embodied in the elements mounted on carriage 62. Accordingly, the ultrasonic application device mounted in the outer working surface of the work drum is the device supplying the ultrasonic energy, rather than the ultrasonic application device mounted on the ultrasonic support subassembly 64.

Alternatively, other energy application devices may be substituted for the ultrasonic devices. Such devices include electric resistance heating elements, electric indicator elements, and fluid heated elements.

Having thus described the invention in full detail, it will be readily apparent that various changes and modifications may be made without departing from the spirit of the invention. All such changes and modifications are contemplated as being within the scope of the present invention, as defined by the following claims.

What is claimed is:

1. An energy system for applying energy to a workpiece, comprising:
   (a) a drum, mounted for rotation about a first axis in a given direction, said drum having a circumferential outer working surface;
   (b) a first energy application device, mounted on said drum at said outer working surface, and extending transverse to the direction of rotation of said drum; and
   (c) a second energy application device, mounted for rotation with said drum, and for moving in a direction transverse to the direction of rotation of said drum to thereby extend over said first energy application device, and operate in combination with said first energy application device, to apply energy to the workpiece at a point moving progressively across the workpiece during rotation of said drum, and for subsequently withdrawing from over said first energy application device during rotation of said drum.

2. An energy system as in claim 1, wherein said first energy application device comprises a first ultrasonic application device, and said second energy application device comprises a second ultrasonic application device, cooperating with said first ultrasonic application device to thereby apply ultrasonic energy to a workpiece on said drum.

3. An energy system as in claim 1, wherein said energy comprises thermal energy generated by electrical resistance.

4. An energy system as in claim 2, said first ultrasonic application device comprising an anvil, and said second ultrasonic application device comprising an ultrasonic horn.

5. An energy system as in claim 4, said anvil comprising a metal bar mounted essentially flush with said outer working surface of said drum.

6. An energy system as in claim 4, said ultrasonic horn being mounted to extend over said anvil, and to subsequently withdraw from over said anvil, during each rotation of said drum.

7. An energy system as in claim 4, said ultrasonic horn being mounted to extend over said anvil, to apply pressure on a workpiece on said anvil, and thereby to apply ultrasonic energy to the workpiece while extended over said anvil.

8. An energy system as in claim 4, said ultrasonic horn being mounted to traverse an energy application path over said anvil and a workpiece on said anvil, the energy application path being oriented transversely across the outer working surface, said ultrasonic system further comprising apparatus for simultaneously applying pressure and ultrasonic energy through said ultrasonic horn, to the workpiece disposed on said anvil, at the point moving progressively across the workpiece, thereby to accomplish work on the workpiece while said ultrasonic horn is so traversing the energy application path and so applying pressure and ultrasonic energy to the workpiece.

9. An energy system as in claim 6, said ultrasonic horn comprising a wheel mounted for rotation about a second axis, to thereby apply ultrasonic energy to the workpiece at the point moving progressively across the workpiece as said ultrasonic horn traverses said energy application path.

10. An energy system as in claim 6, said ultrasonic horn comprising a rotary ultrasonic horn, an energy application path including an outgoing segment of the path wherein said rotary ultrasonic horn is extended over said anvil, and an incoming segment wherein said rotary ultrasonic horn is withdrawn from over said anvil, said ultrasonic system further comprising (a) apparatus for applying pressure through said rotary ultrasonic horn at the point moving progressively across the workpiece as said ultrasonic horn traverses said energy application path, and (b) control apparatus adapted to activate said apparatus for applying pressure, to thereby apply pressure through said rotary ultrasonic horn at the point moving progressively across the workpiece on one of said segments of said energy application path and to withhold the pressure on the other of said segments of said energy application path.

11. An energy system as in claim 7, said ultrasonic horn comprising a rotary ultrasonic horn, an energy application path including an outgoing segment of the path wherein said rotary ultrasonic horn is extended over said anvil, and an incoming segment wherein said rotary ultrasonic horn is withdrawn from over said anvil, said ultrasonic system further comprising (a) apparatus for applying pressure through said rotary ultrasonic horn at the point moving progressively across the workpiece as said ultrasonic horn traverses said energy application path, and (b) control apparatus adapted to activate said apparatus for applying pressure, to thereby apply pressure through said rotary ultrasonic horn at the point moving progressively across the workpiece on one of said segments of said energy application path and to withhold the pressure on the other of said segments of said energy application path.

12. An energy system as in claim 8, said ultrasonic system comprising at least two said anvils mounted at different radial locations about said outer working surface of said drum, and corresponding at least two said rotary ultrasonic horns mounted for rotation with said drum and over respective ones of said at least two anvils, said control apparatus including apparatus for controlling operation of all of said at least two rotary ultrasonic horns such that the respective said rotary ultrasonic horn begins being extended over a respective said anvil when the respective said anvil is disposed at a locus corresponding to a first angle "E" measured with respect to a reference line passing through said first axis of rotation and subsequently withdraws from over the respective said anvil such that said rotary ultrasonic horn is fully withdrawn when said drum has rotated such that the respective said anvil is disposed at a locus corresponding to a second angle "W" measured with respect to the reference line passing through said first axis of rotation, and wherein the same angles "E" and "W" apply for each of said at least two ultrasonic horns.

13. An energy system as in claim 2, said first ultrasonic application device comprising said ultrasonic horn, and said second ultrasonic application device comprising said anvil.

14. An energy system as in claim 13, said ultrasonic horn comprising a flat planar surface plunge-type ultrasonic horn having an ultrasonic working surface mounted essentially flush with said outer working surface of said drum.

15. An energy system as in claim 13, said anvil being mounted to extend over said ultrasonic horn, and to subsequently withdraw from over said ultrasonic horn, during each rotation of said drum.

16. An energy system as in claim 13, said anvil being mounted to extend over said ultrasonic horn, to apply pressure on a workpiece on said ultrasonic horn, and thereby to apply ultrasonic energy to the workpiece while extended over said ultrasonic horn.

17. An energy system as in claim 13, said anvil being mounted to traverse an energy application path over said ultrasonic horn and a workpiece on said ultrasonic horn, and to simultaneously apply pressure and ultrasonic energy on the workpiece disposed on said ultrasonic horn, thereby to accomplish work at the point moving progressively across the workpiece while so traversing said ultrasonic horn.

18. An energy system as in claim 15, said anvil comprising a wheel mounted for rotation about a second axis, such that the combination of said anvil and said ultrasonic horn provides effective ultrasonic energy to the workpiece at the point moving progressively across the workpiece as said anvil traverses an energy application path.

19. An energy system as in claim 15, said anvil comprising a rotary anvil, an energy application path including an outgoing segment of the path wherein said rotary anvil is extended over said ultrasonic horn, and an incoming segment wherein said rotary anvil is withdrawn from over said ultrasonic horn, said ultrasonic system further comprising (a) apparatus for applying pressure through said rotary anvil at the point moving progressively across the workpiece as said anvil traverses said energy application path, and (b) control apparatus adapted to activate said apparatus for applying pressure, to thereby apply pressure through said rotary anvil at the point moving progressively across the workpiece on one of said segments of said energy application path and to withhold the pressure on the other of said segments of said energy application path.

20. An energy system as in claim 16, said anvil comprising a rotary anvil, an energy application path including an outgoing segment of the path wherein said rotary anvil is extended over said ultrasonic horn, and an incoming segment wherein said rotary anvil is withdrawn from over said ultrasonic horn, said ultrasonic system further comprising (a) apparatus for applying pressure through said rotary anvil at the point moving progressively across the workpiece as said anvil traverses said energy application path, and (b) control apparatus adapted to activate said apparatus for applying pressure, to thereby apply pressure through said rotary anvil at the point moving progressively across the workpiece on one of said segments of said energy application path and to withhold the pressure on the other of said segments of said energy application path.

21. An energy system as in claim 17, said energy system comprising at least two said ultrasonic horns mounted at different radial locations about said outer working surface of said drum, and corresponding at least two said rotary anvils mounted for rotation with said drum and over respective ones of said at least two ultrasonic horns, control apparatus including apparatus for controlling operation of all of said at least two rotary anvils such that the respective said rotary anvil begins being extended over a respective said ultrasonic horn when the respective said anvil is disposed at a locus corresponding to a first angle "E" measured with respect to a reference line passing through said first axis of rotation and subsequently withdraws from over the respective said anvil such that said rotary ultrasonic horn is fully withdrawn from over the respective said ultrasonic horn when said drum has rotated such that the respective said ultrasonic horn is disposed at a second angle "W" measured with respect to the reference line passing through said first axis of rotation, and wherein the same angles "E" and "W" apply for each of said at least two ultrasonic horns.

22. An energy system as in claim 1, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said second ultrasonic application device such that said second ultrasonic application device extends over said drum and correspondingly over said first ultrasonic application device and the workpiece while the workpiece traverses said working path, and withdraws from over said drum and said first ultrasonic application device while said working station of said outer working surface traverses from said removing station to said placing station.

23. An energy system as in claim 2, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said ultrasonic horn such that said ultrasonic horn extends over said drum and correspondingly over said anvil and the workpiece while the workpiece traverses said working path, and withdraws from over said drum and said anvil while said working station of said outer working surface traverses from said removing station to said placing station.

24. An energy system as in claim 5, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said ultrasonic horn such that said ultrasonic horn extends over said drum and correspondingly over said anvil and the workpiece while the workpiece traverses said working path, and withdraws from over said drum and said anvil while said working station of said outer working surface traverses from said removing station to said placing station.

25. An energy system as in claim 6, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices, removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said ultrasonic horn such that said ultrasonic horn extends over said drum and correspondingly over said anvil and the workpiece while the workpiece traverses said working path, and withdraws from over said drum and said anvil while said working station of said outer working surface traverses from said removing station to said placing station.

26. An energy system as in claim 7, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said ultrasonic horn such that said ultrasonic horn extends over said drum and correspondingly over said anvil and the workpiece while the workpiece traverses said working path, and withdraws from over said drum and said anvil while said working station of said outer working surface traverses from said removing station to said placing station.

27. An energy system as in claim 8, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said rotary ultrasonic horn such that said rotary ultrasonic horn extends over said drum and correspondingly over said anvil and the workpiece while the workpiece traverses said working path, and withdraws from over said drum and said anvil while said working station of said outer working surface traverses from said removing station to said placing station.

28. An energy system as in claim 10, said energy system further comprising placing apparatus adjacent said drum, at a placing station disposed at an angle "P" measured with respect to a reference line passing through said first axis, for placing workpieces onto working stations of said outer working surface where ultrasonic energy can be applied to the workpieces by said first and second ultrasonic application devices; removing apparatus adjacent said drum, at a removing station disposed at an angle "R" measured with respect to the reference line passing through said first axis, for removing the workpieces from said outer working surface, such that the workpieces traverse a working path on said outer working surface about the circumference of said drum from said placing station to said removing station; and control apparatus for controlling movement of said at least two rotary ultrasonic horns such that said at least two ultrasonic horns extend over said drum and correspondingly over the respective said anvils and the workpieces while the workpieces traverse said working path and are withdrawn from over said drum and said anvils while the respective said working stations of said outer working surface traverse from said removing station to said placing station.

29. An energy system as in claim 11, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said anvil such that said anvil extends over said drum and correspondingly over said ultrasonic horn and the workpiece while the workpiece traverses said working path and is withdrawn from over said drum and said ultrasonic horn while said working station of said outer working surface traverses from said removing station to said placing station.

30. An energy system as in claim 13, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said anvil such that said anvil extends over said drum and correspondingly over said ultrasonic horn and the workpiece while the workpiece traverses said working path and is withdrawn from over said drum and said ultrasonic horn while said working station of said outer working surface traverses from said removing station to said placing station.

31. An energy system as in claim 14, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said anvil such that said anvil extends over said drum and correspondingly over said ultrasonic horn and the workpiece while the workpiece traverses said working path and is withdrawn from over said drum and said ultrasonic horn while said working station of said outer working surface traverses from said removing station to said placing station.

32. An energy system as in claim 15, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said anvil such that said anvil extends over said drum and correspondingly over said ultrasonic horn and the workpiece while the workpiece traverses said working path and is withdrawn from over said drum and said ultrasonic horn while said working station of said outer working surface traverses from said removing station to said placing station.

33. An energy system as in claim 16, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said anvil such that said anvil extends over said drum and correspondingly over said ultrasonic horn and the workpiece while the workpiece traverses said working path and is withdrawn from over said drum and said ultrasonic horn while said working station of said outer working surface traverses from said removing station to said placing station.

34. An energy system as in claim 17, said energy system further comprising placing apparatus adjacent said drum, at a placing station disposed at an angle "P" measured with respect to a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said anvil such that said anvil extends over said drum and correspondingly over said ultrasonic horn and the workpiece while the workpiece traverses said working path and is withdrawn from over said drum and said ultrasonic horn while said working station of said outer working surface traverses from said removing station to said placing station.

35. An energy system for applying energy to a workpiece, comprising:
  (a) a drum, mounted for rotation about a first axis in a given direction, said drum having a circumferential outer working surface;
  (b) a first energy application device, mounted on said drum at said outer working surface, and extending transverse to the direction of rotation of said drum; and
  (c) a second energy application device, mounted for rotation with said drum, and for moving in a direction transverse to the direction of rotation of said drum to thereby extend over said first energy application device, and operate in combination with said first energy application device, to apply energy to the workpiece at a line moving progressively across the workpiece during rotation of said drum, and for subsequently withdrawing from over said first energy application device during rotation of said drum.

36. An energy system as in claim 35, said energy system further comprising placing apparatus adjacent said drum, at a placing station disposed at an angle "P" measured with respect to 1a reference line passing through said first axis, for placing a workpiece onto a working station of said outer working surface where ultrasonic energy can be applied to the workpiece by said first and second ultrasonic application devices; removing apparatus adjacent said drum, at a removing station disposed at an angle "R" measured with respect to the reference line passing through said first axis, for removing the workpiece from said outer working surface, such that the workpiece traverses a working path on said outer working surface about the circumference of said drum from said placing station to said removing station; and control apparatus for controlling movement of said at least two anvils such that said at least two anvils extend over said drum and correspondingly over said ultrasonic horn and the workpiece while the workpiece traverses said working path and is withdrawn from over said drum and said ultrasonic horn while said working station of said outer working surface traverses from said removing station to said placing station.

37. An energy system as in claim 35, said second energy application device being mounted to traverse an energy application path over said first energy application device, the energy application path being oriented transversely across the outer working surface.

38. An energy system as in claim 37, said energy application path including an outgoing segment, said second energy application device applying pressure at the line moving progressively across the workpiece as said second energy application device traverses said energy application path.

39. An energy system as in claim 35, said second energy application device comprising a rotary ultrasonic horn and said first energy application device comprising an anvil.

40. An energy system as in claim 35, said first energy application device comprising an ultrasonic horn and said second energy application device comprising a rotary anvil.

41. An ultrasonic energy system for applying ultrasonic energy to a workpiece, comprising:

(a) a drum, mounted for rotation about a first axis in a given direction, said drum having a circumferential outer working surface;

(b) a first ultrasonic energy application device, mounted on said drum at said outer working surface, and being oriented transverse to the direction of rotation of said drum; and (c) a second rotary ultrasonic energy application device, mounted for rotation with said drum, and for moving in a direction transverse to the direction of rotation of said drum to thereby extend over said first ultrasonic application device, said second rotary ultrasonic energy application device being rotatable about a second axis transverse to the first axis of said drum, to operate in combination with said first ultrasonic energy application device, to apply ultrasonic energy to the workpiece during rotation of said drum and concurrent rotation of said second ultrasonic energy application device.

42. An ultrasonic energy system as in claim 41, said second rotary ultrasonic energy application device comprising a rotary ultrasonic horn.

43. An ultrasonic system as in claim 42, said first ultrasonic energy application device comprising an anvil.

44. An ultrasonic system as in claim 43, said anvil comprising a metal bar mounted essentially flush with said outer working surface of said drum.

45. An ultrasonic energy system as in claim 41, said second rotary ultrasonic energy application device comprising an anvil.

46. An ultrasonic energy system as in claim 45, said first ultrasonic energy application device comprising a flat planar surface plunge-type ultrasonic horn having an ultrasonic working surface mounted essentially flush with said outer working surface of said drum.

47. An ultrasonic energy system as in claim 45, said anvil comprising a wheel, such that the combination of said anvil and said first ultrasonic energy application device provides effective ultrasonic energy to the workpiece at a point moving progressively across the workpiece as said anvil traverses an energy application path.

48. An ultrasonic energy system as in claim 46, said anvil comprising a wheel, such that the combination of said anvil and said first ultrasonic energy application device provides effective ultrasonic energy to the workpiece at a point moving progressively across the workpiece as said anvil traverses an energy application path.

49. An ultrasonic system as in claim 11, said control apparatus being adapted to activate said apparatus for applying pressure, to thereby apply pressure through said rotary ultrasonic horn at the point moving progressively across the workpiece on the outgoing segment of said energy application path.

50. An energy system as in claim 1, said second energy application device moving in a direction transverse to the direction of rotation of said drum while applying energy to the workpiece.

* * * * *